US011589765B2

(12) United States Patent
Costa (10) Patent No.: US 11,589,765 B2
(45) Date of Patent: *Feb. 28, 2023

(54) HEMODYNAMIC PARAMETER (HDP) MONITORING SYSTEM FOR DIAGNOSIS OF A HEALTH CONDITION OF A PATIENT (71) Applicant: TheraBionic, Inc., Winston-Salem, NC (US)

(72) Inventor: Frederico P. Costa, Sao Paulo (BR)

(73) Assignee: THERABIONIC, INC., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/853,173

(22) Filed: Apr. 20, 2020

(65) Prior Publication Data
US 2020/0315466 A1 Oct. 8, 2020

Related U.S. Application Data (63) Continuation of application No. 15/569,312, filed as application No. PCT/US2016/028880 on Apr. 22, (Continued)

(51) Int. Cl.
A61B 5/00 (2006.01)
A61B 5/029 (2006.01)
(Continued)

(52) U.S. Cl.
CPC .............. A61B 5/029 (2013.01); A61B 5/021 (2013.01); A61B 5/0265 (2013.01); A61B 5/352 (2021.01);
(Continued)

(58) Field of Classification Search
CPC ....... A61B 5/029; A61B 5/352; A61B 5/0265; A61B 5/021; A61B 5/02108;
(Continued)

(56) References Cited

U.S. PATENT DOCUMENTS 5,441,528 A 8/1995 Chang et al.
5,501,704 A 3/1996 Chang et al.
(Continued)

FOREIGN PATENT DOCUMENTS

CN 102046069 A 5/2011
CN 103006185 A 4/2013
(Continued)

OTHER PUBLICATIONS

Barbault et al: "Amplitude-Modulated Electromagnetic Fields for the Treatment of Cancer: Discovery of Tumor-Specific Frequencies and Assessment of a Novel Therapeutic Approach", Apr. 14, 2009, J. Exp. Clin. Cancer Res. 28:51-60.
(Continued)

Primary Examiner — Scott M. Getzow
(74) Attorney, Agent, or Firm — Fox Rothschild LLP (57) ABSTRACT A hemodynamic parameter (Hdp) monitoring system for diagnosing a health condition of a patient and for establishing Hdp marker values or Hdp surrogate marker values for purposes of comparison with Hdp values of a patient is provided. An Hdp monitor senses, measures, and records Hdp values exhibited by the patient during a basal or non-exposure period and furthermore Hdp values exhibited by the patient during or after an exposure period during which the patient is exposed to low-energy electromagnetic output signals. An electrically-powered generator is adapted to be actuated to generate said low-energy electromagnetic carrier output signals for exposing or applying to the patient such output signals during said exposure period.

12 Claims, 4 Drawing Sheets

Related U.S. Application Data 2016, now Pat. No. 10,624,546, which is a continuation of application No. 14/545,377, filed on Apr. 28, 2015, now abandoned.

(51) Int. Cl.

| | |
|---|---|
| *A61B 5/0265* | (2006.01) |
| *A61B 5/021* | (2006.01) |
| *A61N 5/02* | (2006.01) |
| *A61N 1/40* | (2006.01) |
| *A61B 5/352* | (2021.01) |
| *A61B 5/02* | (2006.01) |
| *A61B 5/0245* | (2006.01) |
| *A61B 5/0255* | (2006.01) |

(52) U.S. Cl.
CPC ............. *A61N 1/403* (2013.01); *A61N 5/025* (2013.01); *A61B 5/02007* (2013.01); *A61B 5/0245* (2013.01); *A61B 5/0255* (2013.01); *A61B 5/02108* (2013.01); *A61B 5/02141* (2013.01); *A61N 5/022* (2013.01)

(58) Field of Classification Search
CPC ............. A61B 5/02141; A61B 5/0255; A61B 5/02007; A61B 5/0245; A61N 5/025; A61N 1/403; A61N 5/022
See application file for complete search history.

(56) References Cited

U.S. PATENT DOCUMENTS

| | | | |
|---|---|---|---|
| 5,634,939 | A | 6/1997 | Kuster et al. |
| 5,690,692 | A | 11/1997 | Fleming |
| 8,977,365 | B2 | 3/2015 | Pasche et al. |
| 2003/0139678 | A1 | 7/2003 | Hoium et al. |
| 2004/0127944 | A1 | 7/2004 | Casset |
| 2004/0230130 | A1 | 11/2004 | Kuo et al. |
| 2005/0143779 | A1 | 6/2005 | Libbus |
| 2007/0173908 | A1 | 7/2007 | Begnaud |
| 2008/0221419 | A1 | 9/2008 | Furman |
| 2011/0130800 | A1 | 6/2011 | Weinstein et al. |
| 2011/0224565 | A1 | 9/2011 | Ong et al. |
| 2013/0079853 | A1 | 3/2013 | Pasche et al. |
| 2013/0218021 | A1 | 8/2013 | Messano, Jr. et al. |
| 2013/0237875 | A1 | 9/2013 | Blankfield |
| 2014/0303457 | A1 | 10/2014 | Pipke |
| 2016/0116366 | A1 | 4/2016 | Da Silva et al. |
| 2016/0317050 | A1 | 11/2016 | Costa |

FOREIGN PATENT DOCUMENTS

| | | |
|---|---|---|
| EP | 0592851 A2 | 4/1994 |
| EP | 2139557 B1 | 5/2015 |
| JP | 2010-522051 A | 7/2010 |
| JP | 2011-519704 A | 7/2011 |
| JP | 2013539690 A | 10/2013 |
| WO | 9749453 A1 | 12/1997 |
| WO | 2006031331 A1 | 3/2006 |
| WO | 2008116640 A2 | 10/2008 |
| WO | 2008125186 A2 | 10/2008 |
| WO | 2009138881 A2 | 11/2009 |
| WO | 2011135297 A1 | 11/2011 |
| WO | 2016176117 A1 | 11/2016 |
| WO | 2018112413 A1 | 6/2018 |

OTHER PUBLICATIONS

Costa et al: "Treatment of Advanced Hepatocellular Carcinoma with Very Low Levels of Amplitude-Modulated Electromagnetic Fields", Aug. 9, 2011, British Journal of Cancer 105:640-648.

Fortin, et al: "Non-Invasive Beat-to-Beat Cardiac Output Monitoring by an Improved Method of Transthoracic Bioimpedance Measurement", Nov. 2006, Computers in Biology and Medicine 36(11):1185-1203.

Zimmerman et al: "Cancer Cell Proliferation is Inhibited by Specific Modulation Frequencies", Dec. 1, 2012, British Journal of Cancer 106:307-313.

| Time [s] | Beat [1] | RRI [%] | HR [bpm] | sBP [mmHg] | dBP [mmHg] | mBP [mmHg] | SV [ml] | SI [ml/m2] | CO [l/min] | CI [l/(min*m2)] | TPR [dyne*s/cm^5] | TPRI [dyne*s*m2/cm^5] |
|---|---|---|---|---|---|---|---|---|---|---|---|---|
| 103.6 repouso | | | | | | | | | | | | |
| 103.97 | 126 | 737.375 | 81.37 | 115.778 | 78.356 | 88.34 | 74.99 | 51.16 | 6.102 | 4.163 | 1118.865 | 1640.027 |
| 104.71 | 127 | 732.667 | 81.893 | 116.024 | 79.121 | 88.716 | 72.768 | 49.644 | 5.959 | 4.065 | 1150.716 | 1686.715 |
| 105.44 | 128 | 699.708 | 85.75 | 117.968 | 79.841 | 90.539 | 75.722 | 51.659 | 6.493 | 4.43 | 1078.55 | 1580.934 |
| 106.14 | 129 | 714.417 | 83.985 | 117.287 | 79.257 | 90.188 | 76.49 | 52.183 | 6.424 | 4.383 | 1085.773 | 1591.521 |
| 106.85 | 130 | 720.708 | 83.251 | 117.974 | 79.554 | 90.25 | 78.122 | 53.297 | 6.504 | 4.437 | 1073.224 | 1573.127 |
| 107.57 | 131 | 723.083 | 82.978 | 118.362 | 79.537 | 90.408 | 75.45 | 51.474 | 6.261 | 4.271 | 1116.913 | 1637.166 |
| 108.3 | 132 | 748.083 | 80.205 | 118.081 | 79.883 | 90.408 | 74.632 | 50.916 | 5.986 | 4.084 | 1162.254 | 1703.627 |
| 109.05 | 133 | 742.417 | 80.817 | 119.523 | 80.184 | 90.8 | 73.804 | 50.351 | 5.965 | 4.069 | 1177.611 | 1726.138 |
| 109.79 | 134 | 708.375 | 84.701 | 120.338 | 81.216 | 92.126 | 76.541 | 52.218 | 6.483 | 4.423 | 1099.795 | 1612.075 |
| 110.5 | 135 | 719 | 83.449 | 121.008 | 81.189 | 92.583 | 74.16 | 50.593 | 6.189 | 4.222 | 1158.048 | 1697.462 |
| 111.22 | 136 | 724 | 82.873 | 121.297 | 81.053 | 92.628 | 73.693 | 50.275 | 6.107 | 4.166 | 1174.065 | 1720.939 |
| 111.94 | 137 | 747.333 | 80.285 | 121.092 | 80.937 | 91.868 | 71.273 | 48.624 | 5.722 | 3.904 | 1242.439 | 1821.162 |
| 112.69 | 138 | 743.083 | 80.745 | 121.495 | 81.403 | 92.152 | 69.968 | 47.733 | 5.65 | 3.854 | 1262.439 | 1850.478 |
| 113.43 | 139 | 727.417 | 82.484 | 122.391 | 81.995 | 92.983 | 70.292 | 47.955 | 5.798 | 3.956 | 1241.578 | 1819.899 |
| 114.16 | 140 | 702.042 | 85.465 | 123.173 | 82.116 | 94.327 | 72.778 | 49.651 | 6.22 | 4.243 | 1174.627 | 1721.763 |
| 114.86 | 141 | 721.042 | 83.213 | 123.458 | 81.915 | 93.877 | 71.688 | 48.907 | 5.965 | 4.07 | 1218.726 | 1786.403 |
| 115.58 | 142 | 724.375 | 82.83 | 123.854 | 81.843 | 94.14 | 71.02 | 48.452 | 5.883 | 4.013 | 1239.451 | 1816.782 |
| 116.3 | 143 | 749.667 | 80.036 | 123.26 | 82.448 | 93.395 | 70.051 | 47.791 | 5.607 | 3.825 | 1289.837 | 1890.637 |
| 117.05 | 144 | 741.042 | 80.967 | 124.372 | 82.542 | 93.395 | 68.801 | 46.938 | 5.571 | 3.8 | 1309.997 | 1920.188 |
| 117.8 | 145 | 719.042 | 83.444 | 124.628 | 83.005 | 94.219 | 69.902 | 47.689 | 5.833 | 3.979 | 1259.915 | 1846.778 |
| 118.51 | 146 | 705.375 | 85.061 | 124.838 | 82.823 | 94.863 | 73.072 | 49.851 | 6.216 | 4.24 | 1189.248 | 1743.194 |
| 119.22 | 147 | 723.333 | 82.949 | 124.405 | 82.049 | 95.398 | 70.442 | 48.057 | 5.843 | 3.986 | 1249.041 | 1830.839 |
| 119.94 | 148 | 734.75 | 81.66 | 123.712 | 81.95 | 94.229 | 68.693 | 46.864 | 5.609 | 3.827 | 1292.73 | 1894.878 |
| 120.68 | 149 | 740 | 81.081 | 122.918 | 81.689 | 93.644 | 69.571 | 47.463 | 5.641 | 3.848 | 1276.903 | 1871.679 |
| 121.42 | 150 | 739.333 | 81.154 | 122.62 | 81.262 | 93.035 | 69.626 | 47.501 | 5.65 | 3.855 | 1271.551 | 1863.833 |
| 122.16 | 151 | 713.083 | 84.142 | 122.704 | 81.576 | 92.81 | 72.631 | 49.55 | 6.111 | 4.169 | 1182.868 | 1733.842 |
| 122.87 | 152 | 706.75 | 84.896 | 122.272 | 80.537 | 93.36 | 71.491 | 48.773 | 6.069 | 4.141 | 1188.216 | 1741.681 |
| 123.58 | 153 | 721 | 83.218 | 121.519 | 79.867 | 93.145 | 70.458 | 48.068 | 5.863 | 4 | 1216.084 | 1782.53 |
| 124.3 | 154 | 743 | 80.754 | 120.628 | 79.464 | 90.943 | 73.833 | 50.37 | 5.962 | 4.068 | 1179.993 | 1729.628 |

HEMODYNAMIC PARAMETER (HDP) MONITORING SYSTEM FOR DIAGNOSIS OF A HEALTH CONDITION OF A PATIENT

FIELD OF THE INVENTION

This invention relates to a hemodynamic parameter (Hdp) monitoring system for diagnosis, more particularly involving a monitor able to sense and monitor various specified Hdp values and providing recorded values thereof. The recorded specified Hdp values include values required for purposes of performing diagnoses in terms of the invention.

BACKGROUND OF THE INVENTION AND STATE OF THE ART

Various Hdp monitors are available in the art. Such monitors are generally employed to sense and monitor various Hdp values, usually for purposes of diagnosing cardiovascular conditions of a patient. Hdp measurements performed, generally in conjunction with an electrocardiogram (ECG), might include measurements of stroke volume (SV), stroke index (SI) and cardiac output (CO). Such measurements are indicated for the diagnosis and therapy of patients suffering from cardiac conditions such as heart failure, hypertension, coronary artery disease, pericardial disease, obstructive lung and pleural disease and also renal insufficiency. So-called impedance cardiography (ICG), involving application of a fixed current (of about 400 microAmps at 40 kHz) to spaced apart electrodes is described in the literature for purposes of measuring actual patient current. This state of the art is essentially concerned with securing CO measurements and comparisons of the spaced electrode ICG procedure with well-known and regularly employed thermodilution (TD) procedures for measuring CO or calculating such by multiplying stroke volume (SV) with heart-rate (HR).

The state of the art as discussed above has been mentioned in view of this involving passage of current to a patient in the ICG procedure, which procedure, however, is concerned only with attempting to secure, as well as is possible, reliable measurements of CO values of patients. Also of some interest from a state of the art perspective, is mention of direct digital synthesis (DDS) for ensuring stable current sources, which technology may also, but not necessarily, be employed in a component of the hemodynamic monitoring system of the present invention. Further of possible interest from a state of the art perspective, is disclosure of statistical analyses by means of Band-Altman plots of differences between CO measurements provided by different measurement procedures. A Bland-Altman plot (Difference plot) is a method of data plotting used in analyzing the agreement between two different assays, popularized in medical statistics by J. Martin Bland and Douglas G. Altman.

The state of the art as summarized above is to be found in J. Fortin et al./Computers in Biology and Medicine 36 (2006) 1185-1203. This possible interest arises from the present invention involving statistical analyses and computations related to measurements of a variety of specified Hdp values.

Insofar as the present invention is essentially concerned with diagnosing a health condition of a patient, mention of the state of the art as represented by disclosure comprised in EP Application No. 08 734 777.9-1652 related to an electronic system for influencing cellular functions in a warm-blooded mammalian subject, where mention is made of diagnosis in the following terms: "The electronic system of the invention is therefore a valuable diagnostic tool for diagnosing the presence or absence and identities of types of tumor cell growths or cancers". This disclosure, however, does not contemplate or suggest employing measured Hdp values as a means for diagnosis of either a type of cancer or indeed any other form of a health condition of a patient.

In terms of background of the present invention, extensive clinical trials performed with the aid of the electronic system described in above-mentioned EP Application No. 08 734 777.9-1652 led to further investigations related to effects of treatments performed. These further investigations included performing multiple measurements of various Hdp values in patients and determinations, in terms of the present invention, that such values differ dependently of the type of cancer. Such determinations provided basis for proposing a diagnostic procedure based on measured Hdp values for diagnosing a particular form of cancer harbored by a patient. These determinations furthermore suggested that practically any form of a poor health condition suffered by a patient, including such conditions as viral, parasitical or other pathogenic invasions, organ dysfunctions leading to undesirable components such as toxins being comprised in the blood of a patient, drug abuse, poisons, high low-density lipoprotein (LDL) cholesterol levels, venom from a snake-bite and the like, may be diagnosed on the basis of certain identified measured Hdp values patient's diagnosis. Furthermore, since it has previously been determined that Central Nervous System (CNS) disorders described in EP 0 592 851 A2, may be successfully treated by application to a patient of amplitude modulation (AM) carrier signals modulated at predetermined AM frequencies, it is likely that such conditions may be similarly diagnosed on the basis of certain measured Hdp values. Reference is also made to U.S. Pat. No. 5,690, 692 disclosing a lengthy listing of conditions which may be treated with the aid of precise bioactive frequencies. A frequency synthesizer is controlled to generate a specific precise frequency or a series thereof. A keyboard actuated by a user is employed to select such frequencies, which in turn leads to a circuit which gates the generated signal ON or OFF within determined well defined time intervals. Once again, however, influences on Hdp values or determinations thereof are not considered.

Diagnosis in terms of the present invention may be performed with the aid of certain measured and recorded Hdp parameter values measured, in a number of patients pre-diagnosed to be suffering from an identified poor health condition or being in a healthy condition, at determined times and for determined periods, as described in greater detail below.

SUMMARY OF THE INVENTION

A hemodynamic parameter (Hdp) monitoring system for diagnosing a health condition of a patient, for establishing Hdp marker values or Hdp surrogate marker values for purposes of comparison with Hdp values of a patient is provided. An Hdp monitor senses, measures, and records Hdp values exhibited by the patient during a basal or non-exposure period and furthermore Hdp values exhibited by the patient during or after an exposure period during which the patient is exposed to low-energy electromagnetic output signals. An electrically-powered generator is adapted to be actuated to generate said low-energy electromagnetic carrier output signals for exposing or applying to the patient such output signals during said exposure period

BRIEF DESCRIPTION OF THE DRAWING

FIG. 3 is an example is eleven hemodynamic parameters simultaneously measured during each heartbeat:

DETAILED DESCRIPTION OF PREFERRED EMBODIMENTS

The present invention provides hemodynamic parameter (Hdp) monitoring system for diagnosing a health condition of a patient. The system comprises a hemodynamic parameter Hdp monitor that senses and records various identified sensed Hdp values of the patient. The system generally senses various identified sensed Hdp values of the patient utilizing electrodes placed in topical contact with various determined parts of the body. The hemodynamic parameter Hdp monitor further comprises recording means that records the various identified sensed Hdp values of the patient. The recording means can utilize any storage device on which the various identified sensed Hdp values of the patient can be recorded. For purposes of diagnosing a health condition of a patient, it has been determined for purposes of diagnoses performed in accordance with the invention, that a variety of Hdp values need to be sensed, measured and recorded, which include the values of at least the following nine Hdp's:

RR interval (interval from the R peak to the next as shown on an electrocardiogram (ECG) (RRI);
heart rate (HR);
systolic blood pressure (sBP);
diastolic blood pressure (dBP);
median blood pressure (mBP);
pulse pressure (PP);
stroke volume (SV);
cardiac output (CO); and
total peripheral resistance (TPR).

The above initial measurements or values thereof are herein named basal measurements or basal Hdp values. In terms of procedure, initial measurements of above parameters are performed on pre-diagnosed subjects after a period of relaxation, for example about 15 minutes, while the patient is lying in a supine position (face and preferably also palms of the hands facing upwardly).

Following on having performed the above initial measurements, the pre-diagnosed subjects are exposed to or application of an Hdp-influencing procedure involving exposure to or application of selected electromagnetic fields (EMF) output signals. The selection of such output signals would generally be based on output signals predetermined to provide beneficial therapeutic effects in multiple subjects or rather patients pre-diagnosed to be possessed of an identified poor health condition.

The above-mentioned EMF output signals may be provided by a generator device adapted to generate EMF output signals at certain predetermined amplitude modulation (AM) frequencies. The subjects or patients are most preferably exposed to or the output signals are applied to patients during heart-beat times over a determined period of time, most preferably over the time of at least ten heart-beat times of the patient. This procedure would in general take place while the patient remains connected to or is reconnected to the Hdp monitor of the system of the invention so that Hdp values may be sensed and measured during the period of exposure or application. The Hdp values may, however, also or alternatively be sensed and measured after the period of exposures or applications, for purposes of determining potentially lasting effects, generally statistically significant therapeutically beneficial effects, of the exposures or applications to the patient.

The above Hdp values measured during or after above exposures or applications to pre-diagnosed subjects or patients are herein referred to as post-exposure or Hdp variation values.

The procedures above, in general as applied to multiple patients pre-diagnosed to be suffering from an identified form of poor health condition, provide both multiple basal Hdp values and multiple post-exposure Hdp values as related to the identified pre-diagnosed form of poor health condition. These multiple Hdp values, for example for most if not all of the nine Hdp parameters listed above, may in general be somewhat scattered values. Accordingly, for purposes of defining representative marker Hdp values, such scattered values would regularly be analyzed by statistical procedures for purposes of obtaining representative Hdp values for each of the Hdp parameters.

Conventional statistical procedures might for example include Dixon's Q test employed for identifying and rejecting outlier values; a T-test for determining whether or not mean values of two groups of values are statistically different from one another; Fisher's discriminant analysis, standard deviation measures and variance values; and principle component analysis (PCA), a statistical procedure that uses an orthogonal transformation to convert a set of observations of possibly correlated variables into a set of values of linearly uncorrelated variables called principal components. Values reported herein for Hdp values for various Hdp's employ a PCA of correlated variables to linearly uncorrelated variables (PC's). Hdp values analyzed by such statistical procedures serve as markers for so-called surrogate markers employed for diagnosis of a health condition of a subject (including values for a healthy condition). The surrogates in the present invention providing marker values would include numbers of patients pre-diagnosed to be either healthy or suffering from an identified form of a poor health condition, such as an identified form of cancer as mentioned below.

In line with above, the Hdp monitoring system of the present invention, provides means for establishing and identifying marker values for use in diagnosis of health conditions of a patient. The marker values are termed surrogate markers in that the marker values are determined by the monitoring system following on treatments and Hdp value measurements performed on patients pre-diagnosed to be either healthy or suffering from a known form of poor health condition. An Hdp monitor as described above is employed in conjunction with a generator device adapted to generate EM output signals at certain predetermined amplitude modulation (AM) frequencies determined to influence at least certain of the Hdp values of the Hdp's listed above. The Hdp monitoring system of the invention should accordingly include means for sensing and measuring and recording both basal Hdp values and post-exposure Hdp values of patients.

The monitoring system of the invention may furthermore comprise stored information including surrogate markers as described above and comparison means for comparing representative measured Hdp values with representative surrogate markers as described below to provide the indicated diagnosis of a patient undergoing diagnosis. Alternately, the generator device may be adapted to receive sensed basal and post-exposure Hdp values from the Hdp monitor and comprise such stored information, which may, if desired, be communicated to the Hdp monitor to provide the attending medical staff with information concerning the indicated diagnosis.

Representative surrogate markers employed for diagnosis purposes, in terms of the present invention, are derived from computative combinations of information from both representative basal Hdp measured values and representative post-exposure or Hdp variance measured values. Since the predetermined AM frequencies employed for influencing Hdp values are different for each health condition and post exposure Hdp values are similarly different, the computative combinations for deriving representative surrogate markers for a specified health condition requires different computations, for example for purposes of aligning different forms of cancer in a PCA dual group analysis.

The reliability of marker values is of course dependent on the number of pre-diagnosed surrogates included for each type of poor health condition examined. Thus, the incidence of poor health conditions among populations, more particularly high incidence poor health conditions that are difficult to diagnose, such as Hepatocellular Carcinoma (HCC) or related liver diseases, has received particular attention. Similarly, the relatively high incidence of breast cancer has thus far also received particular attention, as reported below.

Post-exposure or Hdp variance measured values, insofar as may be reflected following on exposure to or application of low energy AM carrier signals, in terms of the invention, may be compared with Hdp values which occur following on exposure or application to a patient of predetermined AM frequency values pre-determined to alleviate a cause of a specified poor health condition of a patient. Matching basal and post-exposure Hdp values, on their own, may both support the efficacy of treatment by application of said predetermined AM frequency values and provide a preliminary indication of diagnosis of the health condition of the patient. Reference to the further scientific details related, for example, specifically to two different forms of cancer diagnoses described below. Here, mention is made to patient's diagnosis following on the basal non-exposure period and correlations of patient's diagnosis with hemodynamic patterns in five (83. 3%) of six cases of male HCC, 5 (83. 3%) of six cases of female breast cancer and six (100. 0%) of six healthy controls (Table 4). Similarly, mention is made to tumor-specific hemodynamic response pattern during exposure periods (Table 5)

The electrically powered generator of AM electromagnetic output signals at certain AM frequencies may comprise a storage device for storing predetermined AM frequency values. Such storage device may be employed for controlling the AM frequencies of the output signals, as described in above-mentioned EP Application No. 08 734 777.9-1652.

Alternative to or in addition to comprising a storage device as above, the exposure or application of means for inducing Hdp value variances may comprise a variable AM frequency tuning device adapted to vary the AM frequencies between low and high limit values.

The time periods of exposure or application of AM frequency output signals by means of a variable frequency tuning device within a broad range of frequencies; for example, AM frequencies within a range between from about 0.01 to about 150 MHz, may require a short period of time for Hdp values to be varied at any particular frequency value Thus, consecutive exposures or applications of sections of the range of AM frequencies may be required in order to identify AM frequency values at which post-application Hdp value variations actually occur during the heart-beat times at which Hdp values are sensed, measured and recorded by the Hdp monitor.

The system of the invention includes output signal frequency measurement and recording means for measuring and recording such frequency values at which frequencies Hdp variances of at least certain of the hemodynamic parameter values are exhibited. Similarly, Hdp value recording means for recording each of the measured values for each of the identified Hdp's, preferably separately of one another, measured and recorded before, during or after the period of time of exposure to or application of output signals to the patient.

A further component of the hemodynamic parameter monitoring system of the invention, additional to those described above, is an analyzer component which may be integrated with or coupled to the recording means for recording hemodynamic parameter values before, during or after performing or exposing the patient to a cellular excitation procedure. The analyzer component may include program-controlled calculation means for performing statistical analyses of various of the recorded hemodynamic parameter values to obtain representative values for each of the different recorded hemodynamic parameter values, optionally making a determination of ratios between different representative hemodynamic parameter values, and comparing either or both of such representative values or ratios between different values, with predetermined representative values or ratios, predetermined in patients known to be healthy or to be suffering from or likely to develop an identified poor health condition. The comparison of calculated representative values for recorded hemodynamic parameter values or ratios, more particularly so-called post-excitation hemodynamic parameter variation values, which match with predetermined representative hemodynamic parameter values or ratios, leads to providing an indication of a diagnosis of a health condition of a patient.

An analyzer component may, alternative or additional to being integrated or coupled to the recording means as described above, be located at an analysis center which may perform the analyses based on recorded hemodynamic parameter information received or communicated to the center.

Example 1

Exemplary of the nine different Hdp values recorded during 16 consecutive heart beats are set forth below:

TABLE 1

Hemodynamic Parameter Values Recorded

| Beat | RRI | HR | sBP | dBP | mBP | PP | SV | CO | TPR |
|---|---|---|---|---|---|---|---|---|---|
| 934 | 975.042 | 61.473 | 112.322 | 63.725 | 84.556 | 48.597 | 57.392 | 3 328 | 1849.328 |
| 935 | 993.375 | 60.4 | 112.716 | 63.789 | 85.876 | 48.027 | 52.571 | 3.175 | .2097.994 |
| 936 | 1010.667 | 59.367 | 113.369 | 61.4 | 85.035 | 51.969 | 59.248 | 3.517 | 1865.839 |
| 937 | 633.042 | 94.78 | 110.847 | 70.266 | 82.042 | 40.581 | 58.303 | 5.526 | 1144.283 |

TABLE 1-continued

Hemodynamic Parameter Values Recorded

| Beat | RRI | HR | sBP | dBP | mBP | PP | SV | CO | TPR |
|---|---|---|---|---|---|---|---|---|---|
| 938 | 1249.708 | 48.011 | 111.515 | 57.736 | 82.341 | 53.779 | 61.038 | 2.931 | 2165.934 |
| 939 | 990.417 | 60.581 | 112.166 | 61.945 | 82.065 | 50.221 | 64.365 | 3.899 | 1622 152 |
| 940 | 992.375 | 60.461 | 111.238 | 59.975 | 82.671 | 51.263 | 63.389 | 3.833 | 1663 034 |
| 941 | 937 | 64.034 | 109.904 | 6045 | 79.804 | 48.414 | 63.431 | 4.062 | 1512.71 |
| 942 | 953 | 62.959 | 107.377 | 67.11 | 80.933 | 45.267 | 64.352 | 4.052 | 1538.824 |
| 943 | 974.667 | 61.56 | 111.219 | 62.063 | 53.49 | 49.156 | 67.078 | 4.129 | 1559.211 |
| 944 | 696.375 | 86.16 | 110.614 | 67.459 | 84.906 | 43.155 | 65.59 | 5.651 | 1159.47 |
| 945 | 1214333 | 49.41 | 110.84 | 57.562 | 81.261 | 53.278 | 65.045 | 3.214 | 1948.051 |
| 946 | 935.75 | 60.867 | 109.052 | 62.014 | 79.855 | 47.038 | 66.379 | 4.04 | 1521.775 |
| 947 | 1002.667 | 59.84 | 111.222 | 61.649 | 83.616 | 49.573 | 65.568 | 3.924 | 1643.7 |
| 948 | 600.875 | 95.854 | 111588 | 70.895 | 83.465 | 40.693 | 66.216 | 6.612 | 973.56 |
| 949 | 1281.5 | 46.82 | 107.484 | 54.898 | 78.606 | 52.586 | 59.347 | 2.802 | 2158.584 |
| 950 | 1017333 | 58.978 | 107.438 | 60.7% | 78.335 | 46.642 | 61.743 | 3 641 | 1648.453 |

The above sensed and recorded values for each of the nine hemodynamic parameters are exemplary of such values exhibited by a single patient.

Example 2

The following Table 2 is exemplary Principal Component (PC) values, representative of a multiple number of sensed and recorded hemodynamic parameter values for each of the nine values of a number of patients. The PC representative values are divided into three groups: Pressure, Flow and Beat for three groups each of 8 patients, respectively 8 patients with hepatocellular carcinoma (HCC), 8 patients with breast cancer, and 8 healthy controls for simplifying comparisons of PC Hdp values between patients with a diagnosis of HCC or breast cancer and healthy controls. Also included in the following Table is reference to X and Y canonical coordinates obtained by the Fisher's discriminant analysis, representative pressure, flow and beat PC values of Hdp's exhibited by patients before exposures or applications of EM AM signals:

TABLE 2

Diagnosis based on Hemodynamic parameter (Hdp) linear discriminate and PC Analyses.

| HCC Patient Code | Coordinate X | Coordinate Y | Pressure Principal Components | | | Flow Principal Components | | | Beat Principal Components | | |
|---|---|---|---|---|---|---|---|---|---|---|---|
| | | | P1 | P2 | P3 | F1 | F2 | F3 | B1 | B2 | B3 |
| 55 | −0.405 | −0.032 | 0.932 | −0.056 | 0.016 | 0.205 | 0.376 | 0.061 | −0.01 | −0.011 | 0.001 |
| 56 | −0.39 | −0.024 | 0.688 | −0.041 | 0.094 | 0.124 | 0.337 | 0.012 | 0.002 | 0.004 | −0.001 |
| 59 | −0.418 | −0.021 | 0.699 | 0.068 | 0.069 | 0.214 | 0.125 | 0.291 | 0.003 | 0.002 | −0.012 |
| 60 | −0.411 | −0.02 | 0.634 | 0.058 | 0.031 | 0.249 | 0.326 | 0.007 | −0.002 | .0.002 | −0.001 |
| 62 | −0.377 | −0.017 | 0.87 | 0.044 | 0.139 | 0.211 | 0.309 | 0.029 | −0.009 | −0.002 | 0.003 |
| 77 | −0.388 | 0.006 | 0.781 | −0.115 | 0.038 | 0.119 | 0.344 | 0.019 | −0.002 | −0.002 | 0 |
| 78 | −0.39 | −0.015 | 0.669 | −0.075 | −0.006 | 0.194 | 0.385 | 0.141 | 0.004 | 0.002 | 0 |
| 82 | −0.348 | 41025 | 0.888 | 0.099 | 0.09 | 0.391 | 0.091 | 0.611 | 0.001 | 0 | 0 |
| Breast Cancer | X | Y | P1 | P2 | P3 | F1 | F2 | F3 | B1 | B2 | B3 |
| 39 | 0.327 | −0.033 | 0.804 | −0.007 | 0.044 | 0.172 | 0.337 | 0.044 | −0.001 | −0.001 | 0 |
| 41 | 0.327 | 0.034 | 0.838 | −0.038 | 0.091 | 0.239 | 0.389 | −0.002 | 0.001 | 0.002 | 0.001 |
| 42 | 0.316 | −0.014 | 0.118 | 0.087 | 0.762 | 0.027 | 0.918 | 0.118 | 0 | 0.002 | −0.001 |
| 46 | 0.298 | −0.033 | 0.863 | 0.103 | 0.054 | 0.268 | 0.088 | 0.318 | −0.008 | 0.002 | 0.004 |
| 48 | 0.292 | 0.024 | 0.883 | 0.067 | −0.049 | 0.127 | 0.001 | 0.323 | −0.003 | −0.018 | −0.023 |
| 47 | 0.205 | −0.021 | 0.838 | 0.002 | −0.221 | 0.193 | 0.034 | 0.324 | 0.015 | −0.014 | 0.059 |
| 48 | 0.299 | .0.025 | 0.882 | 0.088 | 4.134 | 0.189 | 0.048 | 0.349 | 0.001 | 0 | 0 |
| 49 | 0.324 | −0.032 | 0.849 | −0.069 | 0.068 | 0.226 | 0.378 | 0.047 | 0 | −0.002 | 0.001 |
| Healthy Individuals | X | Y | P1 | P2 | P3 | F1 | F2 | F3 | B1 | B2 | B3 |
| 4 | −0.275 | 0.002 | 0.231 | 0.815 | −0.01 | 0.054 | 0.099 | 0.337 | −0001 | 0.008 | −0.003 |
| 7 | −0.234 | 0.037 | 0.962 | 0.267 | −0.089 | 0.154 | 0.148 | 0.342 | 0.009 | 0 | 0 |
| 12 | −0.255 | 0.043 | 0.351 | 0.211 | 0.507 | 0.278 | −0.258 | 0.128 | −0.003 | −0.008 | −0.001 |
| 13 | −0.32 | 0.052 | 0.917 | 0.005 | 0.024 | 0.251 | 0.382 | 0.082 | 0.003 | 0.001 | 0 |
| 17 | −0.591 | 0.015 | 0.731 | −0.095 | 0.14 | 0.094 | 0.352 | .0.029 | −0.001 | −0.002 | −0.001 |
| 23 | −0.572 | 0.014 | 0.872 | 0.106 | −0.035 | 0.213 | 0.234 | 0.374 | −0.005 | 0.003 | −0.015 |
| 75 | −0.341 | 0.003 | 0.103 | 0.807 | −0.222 | 0.197 | 0.141 | 0.297 | 0.002 | 0.07 | 0.027 |
| 79 | −0.344 | 0.007 | 0.258 | 0.72 | −0.014 | .0.042 | 0151 | 0.348 | −0.002 | 0.010 | 0.003 |

Of interest from the above figures is firstly that all patients with a diagnosis of cancer, in this example both patients with diagnosis of HCC and patients with diagnosis of breast cancer reflect P1 PC values which are significantly greater than the P2 PC values.

Example 3

The following Table 3 is exemplary discrimination by analytical geometry using canonical coordinates and vectors obtained from PC values, representative of a multiple number of sensed and recorded hemodynamic parameter values for each of the nine values of a number of patients. The PC representative values are divided into three groups, Pressure, Flow and Beat for three groups each of the patients, respectively with HCC, patients with breast cancer, and healthy controls. For determining the generalized squared distance to d group of values using linear discriminant function of geometric parameters, the distinct group of patients based on their diagnosis is identified:

TABLE 3

Diagnosis based on hemodynamic parameter (Hdp), linear discriminant and geometry analyses.

| d_group | Cancer | Healthy | |
|---|---|---|---|
| Cancer | 0 | 120.4929 | |
| Healthy | 120.49729 | 0 | |
| LDA constant | −0.89418 | −68.98654 | |
| Area of triangle | 0.0171 | 0.33941 | |
| Apotema P-B | −0.15385 | −3.18876 | |
| Apotema B-F | 0.040858 | 2.7007 | |
| Apotema F-P | −0.00324 | 0.65841 | |
| Area of circle | −0.001 | −0.0002086 | |

| d_group | HCC | Cancer | Healthy |
|---|---|---|---|
| HCC | 0 | 0.96372 | 119.23965 |
| Cancer | 0.96372 | 0 | 118.8079 |
| Healthy | 119.23965 | 118.8079 | 0 |
| LDA constant | −1.56828 | 0.58072 | −68.04536 |
| Area of triangle | 0.0159 | 0.01738 | 0.33439 |
| Apotema P-B | −0.07174 | −0.19523 | −3.12901 |
| Apotema B-F | 0.4447 | 0.37987 | 2.66957 |
| Apotema F-P | 0.03225 | −002252 | 0.6553 |
| Area of circle | −0.00176 | −0.0005698 | −0.0003422 |

Figure 1:
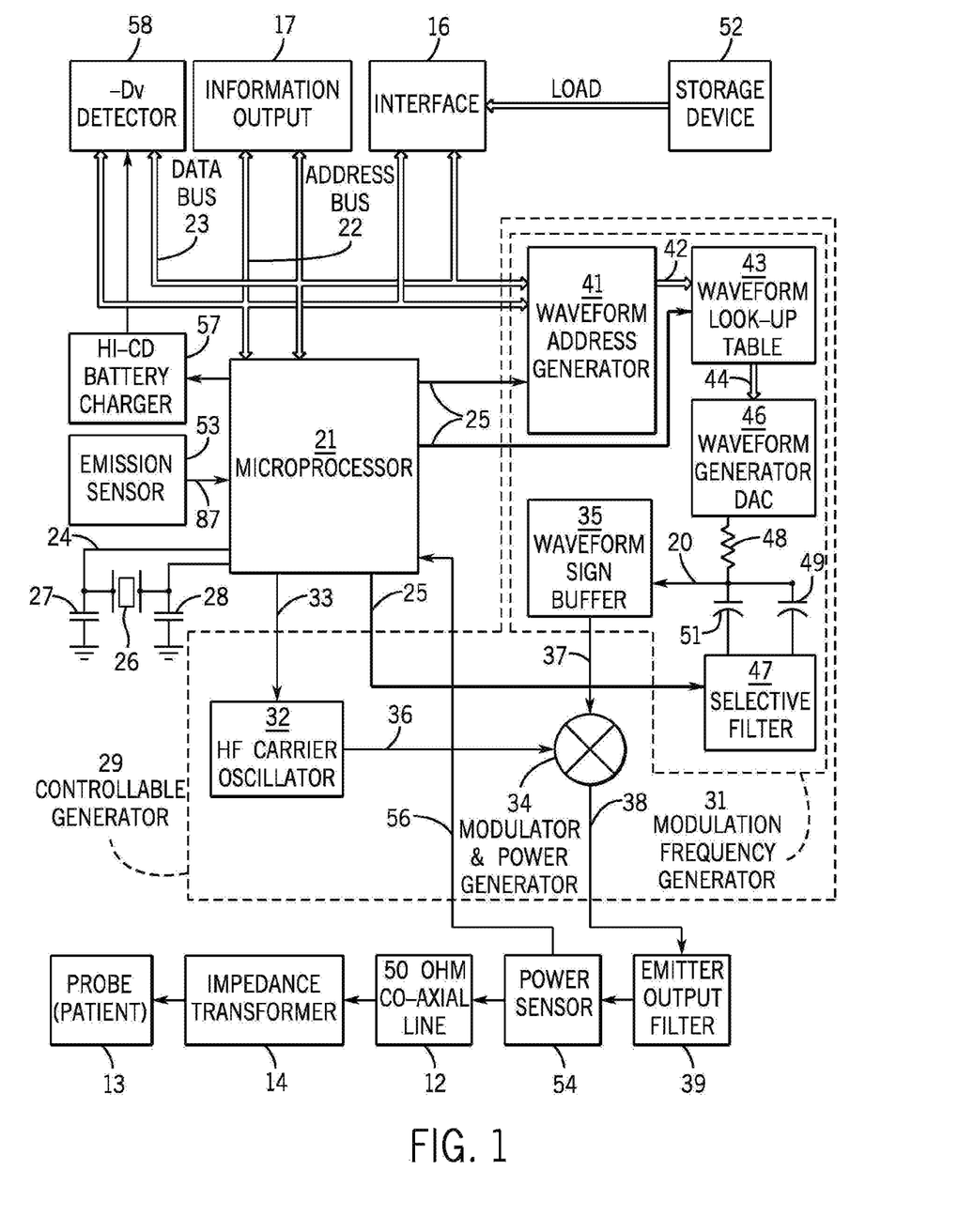
FIG. 1 shows a block diagram of exemplary circuitry, exemplary of circuitry which may be employed as the variable Hdp variation means for application of electromagnetic output signals to a patient in accordance with the present invention.

Referring to FIG. 1, a block diagram of exemplary circuitry, exemplary of circuitry which may be employed as the variable Hdp variation means for application of electromagnetic output signals to a patient is seen. Such exemplary circuitry may be provided with connection means for connection to or may be comprised or integrated into in the hemodynamic parameter monitoring system of the invention. Descriptions of each of the blocks of the block diagram or functions thereof are included to facilitate an understanding thereof.

The block diagram of electronic circuitry of an application system applies AM RF output signals to a patient at predetermined selected AM frequencies. The predetermined selected frequencies are controlled by AM frequency values stored in storage device 52. The stored predetermined AM frequency values are separately determined by biofeedback procedures performed on patients and stored in storage device 52. Various predetermined selected AM frequencies applied to a patient are indicated for treatment of patients suffering from one or other form of a poor health condition of a patient.

Extended clinical trials performed with the aid of above application system led to a discovery that cancerous cell growth or proliferation thereof in patients may be inhibited by application to patients of AM output signals at certain well-defined frequencies. Further investigations revealed that the AM frequencies for purposes of cancer treatment need to be very accurately controlled. Patent Applications filed on a world-wide basis, such as represented by EP 08 734 777. 9 or PCT EP 2008 002 379, International Publication WO 2008 116 640 A2, related to this discovery and investigations, including the identity of very accurate AM frequency values of output signals for identified forms of cancer and a modified system enabling application to a patient of such very accurately controlled AM frequency output signals. The modification to the system comprised in EP 08 734 777.9 includes a so-called Digital Direct Synthesizer (DDS) which may be combined with the illustrated microprocessor 21.

The present invention contemplates employing a device or modified device as described above or indeed other devices described in the art, such as described U.S. Pat. No. 5,690,692 assigned to Regeneration Technology of Tijuana, Mexico, in combination with a hemodynamic parameter monitoring system able to sense and measure at least the nine hemodynamic parameter values referred to above. More particularly, such a combination enables sensing of hemodynamic parameter values of a patient both prior to, during or after application to the patient of AM RF electromagnetic signals as described in prior literature or other such signals as may be applied to the patient. Of particular interest in this regard is that sensed, measured and recorded hemodynamic parameter (Hdp) values differ dependently of the patient condition. For example, as exemplified above, sensed and recorded hemodynamic parameter values differ between patients suffering from different forms of cancer and differ from such values of healthy patient conditions. Moreover, it appears that such hemodynamic parameter values are shared, at least to a major extent, by patients suffering from the same or a closely related poor health condition. The sensed and recorded hemodynamic parameter values accordingly offer diagnosis opportunities for diagnosing various forms of poor health conditions of a nature such as mentioned above and also diagnosis of healthy patient conditions.

Additional to the combination of the invention as discussed above, modifications to the treatment devices or systems described in prior art disclosures are contemplated in terms of the present invention. More particularly, following on determinations of sensed and recorded 11 dp values made in a large variety of patients which have been treated with the aid of earlier systems, it is considered that the requirements for generating specific precise frequencies or a series of precise programmed frequencies may be replaced or supplemented by a variable frequency tuning device, variable between lower and upper frequency limits, which is activated during a time that a patient is connected to a hemodynamic parameter monitor of the nature described.

The availability of such a variable frequency tuning device, in combination with the hemodynamic parameter monitor, would enable sensing of Hdp values required in terms of the invention at various frequency values. The frequency values may be selected from frequency values suggested in terms of prior disclosures for determining the effects on Hdp values or variations thereof. However, such frequency values at which Hdp values or variations thereof which are of interest may be recorded. Recorded frequency values may be compared to predetermined frequency values proposed in earlier disclosures for treatment of patients in support of the identity or accuracy thereof or may provide information related to additional frequency values which may provide beneficial therapeutic effects on patients suffering Tom a poor health condition.

Availability of a variable frequency tuning device, available for varying the frequency of low energy AM output signals during the time of exposure or application of Hdp variation means to a patient is a modification considered may be of practical importance. Thus, in contrast to treatment devices disclosed in prior literature, the frequencies employed for various treatments of patients are invariably predetermined stored frequencies. In this regard, above-mentioned U.S. Pat. No. 5,690,692 might be considered to suggest availability of a frequency tuning device following on disclosure of " . . . the frequency signal is gradually increased at a predetermined rate from zero to a predetermined level controllable by a user." In fact, what is here being referred to is gradual increase of variable amplitudes of signals and not frequencies of amplitude modulations or simply the frequency that the described square wave output signals occur. As in other prior literature, U.S. Pat. No. 5,690,692 relies on predetermined frequency values for performing treatment procedures.

Referring back to FIG. 1, microprocessor 21 operates as the controller for the application system and is connected to control the various components of the system through address bus 22, data bus 23 and input/output (110) lines 25. Microprocessor 21 preferably includes internal storage for the operation code, control program, and temporary data. In addition, microprocessor 21 includes input/output (I/O) ports and internal timers. Microprocessor 21 may, for example, be an 8-bit single-chip micro-controller, 8048 or 8051 available from Intel Corporation, 2200 Mission College Boulevard, Santa Clara, Calif. 95054 U. S. The timing for microprocessor 21 is provided by system clock 24 which includes a clock crystal 26 along with capacitors 27 and 28. System clock 24 may run at any clock frequency suitable for the particular type of microprocessor used. In accordance with one embodiment, system clock 24 operates at a clock frequency of 8.0 MHz.

In general, microprocessor 21 functions to control controllable electromagnetic energy generator circuit 29 to produce a desired form of modulated low energy electromagnetic emission for application to a patient through probe 13. Controllable generator circuit 29 includes modulation frequency generator circuit 31 and carrier signal oscillator 32. Microprocessor 21 operates to activate or de-activate controllable generator circuit 29 through oscillator disable line 33. Controllable generator circuit 29 also includes an AM modulator and power generator 34 which operates to amplitude modulate a carrier signal produced by carrier oscillator 32 on carrier signal line 36, with a modulation signal produced by modulation signal generator circuit 31 on modulation signal line 37. Modulator 34 produces an amplitude modulated carrier signal on modulated carrier signal line 38, which is then applied to the filter circuit 39. The filter circuit 39 is connected to probe 13 via coaxial cable 12 and impedance transformer 14.

Microprocessor 21 controls modulation signal generator circuit 31 of controllable generator circuit 29 through address bus 22, data bus 23 and I/O lines 25. In particular, microprocessor 21 selects the desired waveform stored in modulation waveform storage device 43 via I/O lines 25. Microprocessor 21 also controls waveform address generator 41 to produce on waveform address bus 42 a sequence of addresses which are applied to modulation signal storage device 43 in order to retrieve the selected modulation signal. The desired modulation signal is retrieved from wave form look-up table 43 and applied to modulation signal bus 44 in digital form. Modulation signal bus 44 is applied to digital to analog converter (DAC) 46 which converts the digital modulation signal into analog form. This analog modulation signal is then applied to selective filter 47 which, under control of microprocessor 21, filters the analog modulation signal by use of a variable filter network including resistor 48 and capacitors 49 and 51 in order to smooth the wave form produced by DAC 46 on modulation signal line 20.

In the present embodiment, the various modulation signal wave forms are stored in look-up table 43. With a 2 kilobyte memory, look-up table 43 may contain up to 8 different modulation signal wave forms. Wave forms which have been successfully employed include square wave forms or sinusoidal wave forms. Other possible modulation signal wave forms include rectified sinusoidal, triangular, and combinations of all of the above.

In the present embodiment, each modulation signal wave form uses 256 bytes of memory and is retrieved from look-up table 43 by running through the 256 consecutive addresses. The frequency of the modulation signal is controlled by how fast the wave form is retrieved from look-up table 43. In accordance with the present embodiment, this is accomplished by downloading a control code from microprocessor 21 into programmable counters contained within wave form address generator 41. The output of the programmable counters then drive a ripple counter that generates the sequence of 8-bit addresses on the wave form address bus 42.

Wave form address generator 41 may, for example, be a programmable timer/counter uPD65042C, available from NEC. Modulation signal storage device or look-up table 43 may, for example, be a type 28C16 Electrical Erasable Programmable Read Only Memory (EEPROM) programmed with the desired wave form table. Digital to analog converter 46 may, for example, be a DAC port, AD557IN available from Analog Devices, and selective filter 47 may be a type 4052 multiplexer, available from National Semiconductor or Harris Semiconductor.

The particular modulation control information used by microprocessor 21 to control the operation of controllable generator circuit 29, in accordance with the present invention, is stored in application storage device 52 or, in terms of the present invention may be a variable AM frequency tuning device adapted to load the interface 16 with AM frequencies between and high and low frequency levels. Application storage device 52 may be any storage device capable of storing information for later retrieval. For example, application storage device 52 may be, for example, a magnetic media based storage device such as a card, tape, disk, or drum. Alternatively, application storage device 52 may be a semiconductor memory-based storage device such as an erasable programmable read only memory (EPROM), an electrical erasable programmable read only memory (EEPROM) or a non-volatile random access memory (RAM.). Another alternative for application storage device 52 is a mechanical information storage device such as a punched card, cam, or the like. Yet another alternative for application storage device 52 is an optical storage device such as a compact disk read only memory (CD ROM).

It should be emphasized that although the figures illustrate microprocessor 21 separate from application storage device 52, microprocessor 21 and application storage device 52 may both be incorporated into a single device, which is loaded into the system to control the operation of the system as described herein. In this case, interface 16 would exist between the combination of microprocessor 21 and application storage device 52 and the rest of the system.

Interface 16 is configured as appropriate for the particular application storage device 52 in use. Interface 16 translates the control information stored in application storage device 52 into a usable form for storage within the memory of microprocessor 21 to enable microprocessor 21 to control controllable generator circuit 29 to produce the desired modulated low energy emission. Interface 16 may directly read the information stored on application storage device 52, or it may read the information through use of various known communications links. For example, radio frequency, microwave, telephone or optical based communications links may be used to transfer information between interface 16 and application storage device 52. When application storage device 52 and microprocessor 21 are incorporated in the same device, interface 16 is configured to connect microprocessor 21 to the rest of system.

The control information stored in application storage device 52 specifies various controllable parameters of the modulated low energy RF electromagnetic emission which is applied to a patient through probe 13. Such controllable parameters include, for example, the frequency and amplitude of the carrier, the amplitudes and frequencies of the modulation of the carrier, the duration of the emission, the power level of the emission, the duty cycle of the emission (i. e., the ratio of on time to off time of pulsed emissions applied during an application), the sequence of application of different modulation frequencies for a particular application, and the total number of treatments and duration of each treatment prescribed for a particular patient.

For example, the carrier signal and modulation signal may be selected to drive the probe 13 with an amplitude modulated signal in which the carrier signal includes spectral frequency components below 1 GHz, and preferably between 1 MHz and 900 MHz, and in which the modulation signal comprises spectral frequency components between 0.1 Hz and 10 KHz, and preferably between 1 Hz and 150 KHz. In accordance with the present invention, one or more modulation frequencies may be sequenced to form the modulation signal.

As an additional feature, an electromagnetic emission sensor 53 may be provided to detect the presence of electromagnetic emissions at the frequency of the carrier oscillator 32. Emission sensor 53 provides to microprocessor 21 an indication of whether or not electromagnetic emissions at the desired frequency are present. Microprocessor 21 then takes appropriate action, for example, displaying an error message on information output display 17, disabling controllable generator circuit 29, or the like.

The invention also includes a power sensor 54 which detects the amount of power applied to the patient through probe 13 compared to the amount of power returned or reflected from the patient. This ratio is indicative of the proper use of the system during a therapeutic session. Power sensor 54 applies to microprocessor 21 through power sense line 56 an indication of the amount of power applied to patient through probe 13 relative to the amount of power reflected from the patient.

The indication provided on power sense line 56 may be digitized and used by microprocessor 21, for example, to detect and control a level of applied power, and to record on application storage device 52, information related to the actual treatments applied. Such information may then be used by a physician or other clinician to assess patient treatment compliance and effect. Such treatment information may include, for example: the number of treatments applied for a given time period; the actual time and date of each treatment; the number of attempted treatments; the treatment compliance (i. e., whether the probe was in place or not in place during the treatment session); and the cumulative dose of a particular modulation frequency.

The level of power applied is preferably controlled to cause the specific absorption rate (SAR) of energy absorbed by the patient to be from 1 microwatt per kilogram of tissue to 50 Watts per kilogram of tissue. Preferably, the power level is controlled to cause an SAR of from 100 microwatts per kilogram of tissue to 10 Watts per kilogram of tissue. Most preferably, the power level is controlled to deliver whole body mean SAR in the range of only 0.2 to 1 in W/kg, with a 1 g peak spatial SAR between 150 and 350 mW/kg These SARs may be in any tissue of the patient. The system also includes powering circuitry including battery and charger circuit 57 and battery voltage change detector 58.

In that an association, combination or use of a device of the nature described above in conjunction with a hemodynamic parameter monitoring device enabling sensing, measuring and recording the at least nine parameter values mentioned, before, during or after exposure or application of Hdp influencing means has provided for previously unknown methods of diagnosing health conditions of a patient, further scientific details related, for example, specifically to two different forms of cancer diagnoses are provided below:

INTRODUCTION

The identification of changes in pulse amplitude in patients with a diagnosis of cancer when exposed to low and safe levels of 27.12 MHz radiofrequency electromagnetic fields amplitude-modulated at specific frequencies have previously been reported. (Barbault, A. et al. Amplitude-modulated electromagnetic fields for the treatment of cancer: discovery of tumor-specific frequencies and assessment of a novel therapeutic approach. J. Exp. Clin. Cancer Res. 28, 51, doi:10. 1186/1756-9966-28-51 (2009)). The observation that changes in pulse amplitude occur at exactly the same frequencies in patients with the same type of cancer led to a hypothesis that each type of cancer possesses a specific frequency signature. (Id.) In vitro experiments have shown that tumor-specific frequencies have anti-proliferative effects on cancer cells, modulate the expression of genes involved in cell migration and invasion, and are capable of disrupting the mitotic spindle. (Zimmerman, J. W. et al. Cancer cell proliferation is inhibited by specific modulation frequencies. British Journal of Cancer 106, 307-313 (2012)). The clinical activity of these tumor-specific frequencies was assessed in two separate studies in which patients were treated with intrabuccally administered AM RF EMF, which were modulated at tumor-specific frequencies. Antitumor activity was observed in patients with metastatic breast cancer (Barbault, A. et al. (2009)) and advanced hepatocellular carcinoma (Costa, F. P. et al. Treatment of advanced hepatocellular carcinoma with very low levels of amplitude-modulated electromagnetic fields. British Journal of Cancer 105, 640-648 (2011)) and stable disease was observed in patients with other tumor types.

This study was designed to test the hypothesis that analysis of changes in hemodynamic parameters upon exposure to tumor-specific frequencies is a novel, non-invasive cancer diagnostic approach.

Materials and Methods

The experimental procedures described below were reviewed and approved by the Hospital Sirio Lib anes Institutional Review Board (IRB), Rua Dona Adma Jafet, 50 Conj. 41/43, Sao Paulo SP 01.308-050 Brazil. All patients and healthy individuals enrolled in this study signed an informed consent, which was approved by the IRB. The protocol was registered prior to enrolment of the 1st patient: clinicaltrial.gov identified no. NCT 01686412. 87 individuals were screened and 82 individuals were prospectively enrolled. The discovery group consisted of eight patients with a diagnosis of advanced HCC, six patients with a diagnosis of advanced breast cancer, and six healthy controls. The patient's diagnosis and the nature of AM RF EMF exposure (HCC-specific, breast cancer specific, and randomly chosen frequencies) were disclosed before computational analysis. The validation group consisted of 25 patients with biopsy-proven cancer (11 with advanced HCC and 14 with advanced breast cancer), and 31 healthy controls. The last group consisted of six patients with potentially resectable HCC Three separate groups of patients and healthy controls were analyzed in this study: 1) The discovery group consisted of eight patients with advanced hepatocellular carcinoma, six patients with advanced breast cancer, and six healthy controls; 2) The validation group consisted of 25 patients with a diagnosis of cancer (14 female patients with advanced breast cancer and 11 male patients with advanced HCC) and 31 healthy controls (18 females and 13 males); and 3) six patients (five males and one female) with potentially resectable hepatocellular carcinoma.

Intrabuccal Administration of AM RF EMF:

The AM RF EMF device used for this study has been described in detail previously. (Costa, F. P. et al. British journal of cancer 105, 640-648 (2011)). While patients receiving treatment with AM RF EMF are exposed to three daily one hour treatments, the diagnostic feasibility of AM RF EMF administration was tested during a single 10 minute exposure in order to expose all individuals once to each of the 194 tumor-specific frequencies (HCC specific and breast cancer specific), which are each emitted for three seconds. (Barbault, A. et al. J. Exp. Clin. Cancer Res. 28, 51, doi:10.1186/1756-9966-28-51 (2009); Zimmerman, J. W. et al. British Journal of Cancer 106, 307-313 (2012); Costa, F. P. et al. British Journal of Cancer 105, 640-648 (2011)). Similarly, 194 of the previously reported 236 randomly chosen frequencies were selected (Zimmerman, J. W. et al. British Journal of Cancer 106, 307-313 (2012) to match the number and exposure duration of tumor-specific frequencies. Hence, each individual was exposed to all frequencies included in each of the treatment programs (HCC specific, breast cancer specific, and randomly chosen frequencies), i.e. each modulation frequency emitted for three seconds from the lowest to the highest frequency as previously described. ((Barbault, A. et al. J. Exp. Clin. Cancer Res. 28, 51, doi:10.1186/1756-9966-28-51 (2009); Zimmerman, J. W. et al. British journal of cancer 106, 307-313 (2012); Costa, F. P. et al. British journal of cancer 105, 640-648 (2011)).

Figure 2:
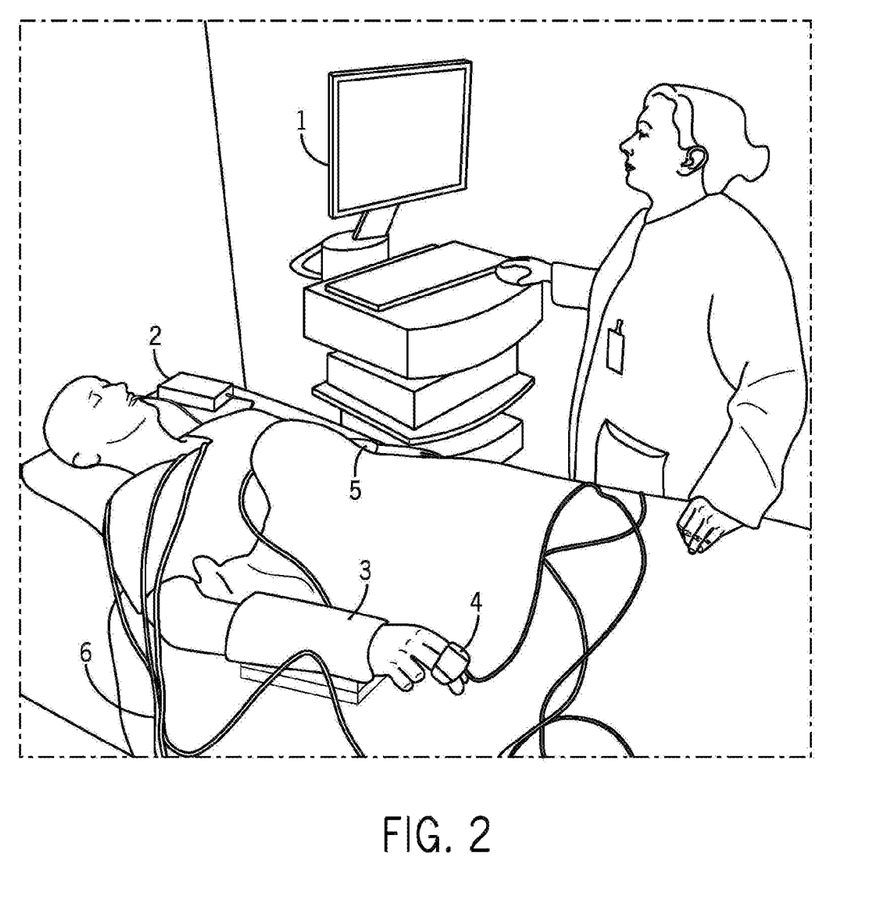
FIG. 2 shows an example patient during experimental setup for continuous monitoring of hemodynamic parameters before and during AM RF EMF exposure in accordance with the present invention.

Hemodynamic Parameter Monitoring:

Referring to FIG. 2, an example patient is seen during experimental setup for continuous monitoring of hemodynamic parameters before and during AM RF EMF exposure. Non-invasive hemodynamic measurement was performed using a Task Force Monitor (CNSystems Medizintechnik GmbH, version 2.2. 12.0, ReininghausstraBe 13, 8020 Graz, Austria). Numerical values of heart rate, blood pressure and blood flow are measured by digital photoplethysmography, pressure cuff and ECG. The hemodynamic parameters are transformed into absolute values for each consecutive heartbeat before and during AM RF EMF exposure. The spoon-shaped antenna for intrabuccal administration of AM RF EMF was placed in the patient's mouth during the entire experiment. In FIG. 2, the Task Force® monitor is labelled 1. The AM RF EMF emitting device is labelled 2. The AM RF EMF emitting device connected to a coaxial cable, which is connected to the spoon-shaped antenna 3. A right arm digital pressure cuff is labelled 4. A digital photoplethysmography is labelled 5. A left arm digital pressure cuff is labelled; 6. Electrodes' cables for ECG and impedance cardiography are provided.

Numerical values of heart rate variability, blood pressure, baroreceptor sensitivity and blood pressure were measured by digital photoplethysmography and ECG acquired through three thoracic adhesive electrodes for high resolution for RR interval analysis. Digital pressure cuff was placed on the right arm and around the middle phalanx of the third and fourth right finger and another on the left arm between the shoulder and the elbow. Blood pressure measurements were transformed into absolute values for each consecutive heartbeat.

Referring to FIG. 3, an example is seen of eleven hemodynamic parameters simultaneously measured during each heartbeat: heart rate (HR), systolic blood pressure (sBP), median blood pressure (mBP), diastolic blood pressure (dBP), total peripheral resistance (TPR), total peripheral resistance index (TPRI), cardiac output (CO), cardiac index (CI), RR interval (RRI), stroke volume (SV), and systolic index (SI). Hemodynamic recording was performed continuously in supine position before and during exposure to AM RF EMF. A total of three million hemodynamic parameters were analyzed in this study.

Participants held the spoon-shaped antenna in their mouth during the entire experiment. The three different devices each programmed with one of the treatment programs (HCC specific, breast cancer specific, and randomly chosen frequencies) were connected prior to initiation of each of the AM RF EMF exposure period. The protocol was conducted in a double-blind fashion.

Figure 4:
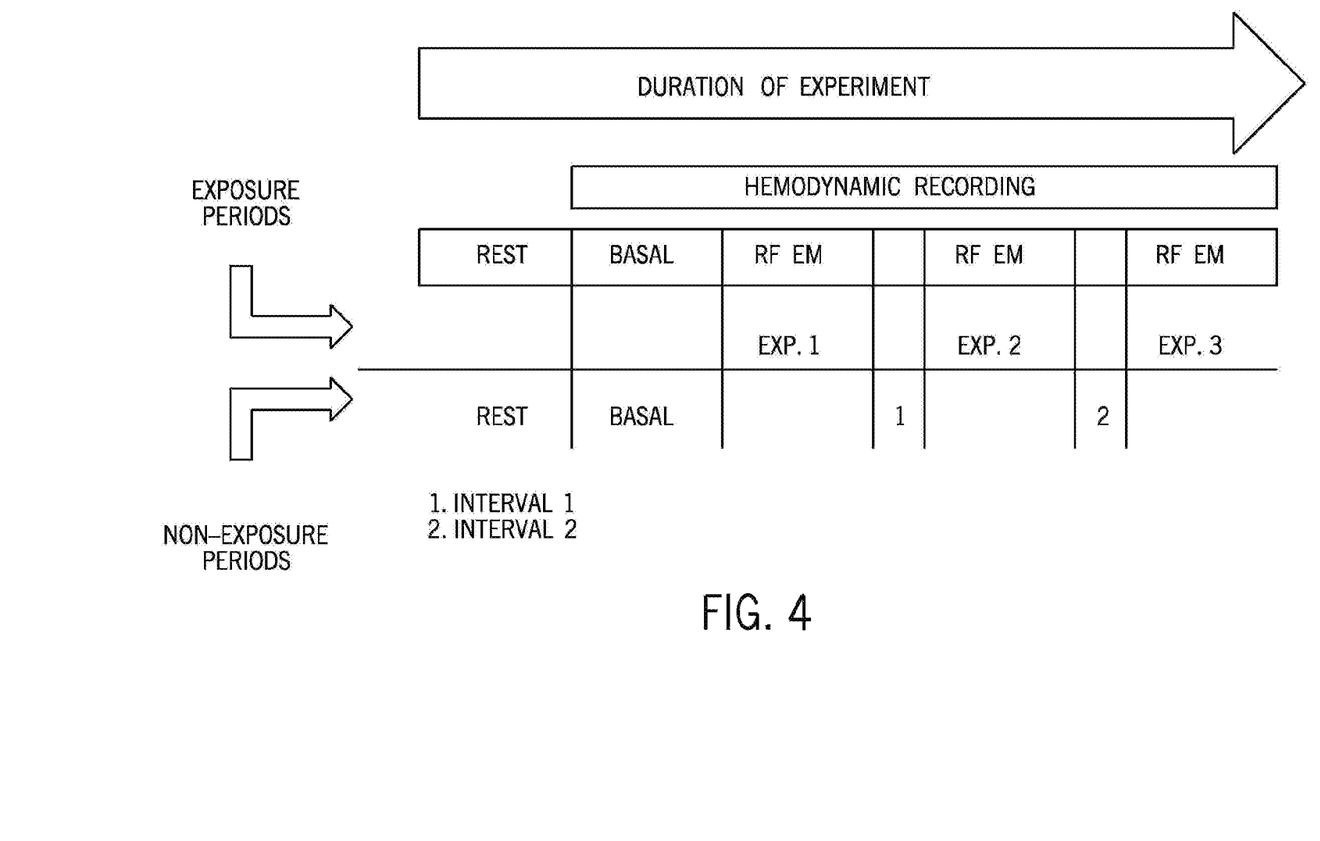
FIG. 4 is a flow diagram representing a hemodynamic recording performed continuously during non-exposure and exposure periods in a double-blind fashion.

Referring to FIG. 4, hemodynamic recording was performed continuously during non-exposure and exposure periods in a double-blind fashion. The non-exposure periods were the initial basal and five minute resting intervals between RF EMF exposures. During the exposure periods, patients received AM RF EMF (HCC-specific, breast cancer-specific, randomly chosen frequencies).

Computational Analysis:

Hemodynamic parameters were analyzed according to three factors: diagnosis (HCC, breast cancer, healthy control), gender, and recording period (baseline and exposure to HCC-specific, breast cancer-specific, and randomly chosen modulation frequencies).

Analysis of the recorded hemodynamic data was only conducted after completion of patient accrual. Data analysis began with the discovery group (six healthy controls, six patients with advanced HCC, and six patients with advanced breast cancer). The anticipated outcome of the discovery group analysis was the creation of computative specific for patients with hepatocellular carcinoma, patients with breast cancer, and healthy controls. Once the computations were constructed, the data from the validation group was analyzed in a blinded fashion in order to validate the computative.

Analysis of six patients diagnosed with potentially resectable HCC was conducted after the completion of the validation group analysis. These patients underwent the same non-invasive hemodynamic parameter measurements within 24 hour prior to HCC surgical resection and after complete recovery within four to six weeks post-surgery. Pre-vs post-surgical analysis was conducted.

Results

Discovery Group
Hemodynamic Pattern Identification Based on Diagnosis
Analysis of Baseline Measurements:

Analysis of hemodynamic parameters during the basal non-exposure period was significantly different among six male healthy controls, six patients with hepatocellular carcinoma, and six female patients with breast cancer in the "Discovery Group" (p<0.0001). Having observed significant differences in hemodynamic parameters between male and female participants and taking into account the fact that the first six patients with HCC were male, two female patients with HCC were transferred from the validation group to the discovery group prior to the analysis of the validation group.

Discovery of Patient's Hemodynamic Pattern:

Hemodynamic parameter analysis during the basal non-exposure period revealed four different hemodynamic patterns in the discovery group. The patient's diagnosis correlated with hemodynamic pattern in 5 (83.3%) of six cases of male HCC, 5 (83.3%) of six cases of female breast cancer and six (100.0%) of six healthy controls, seen in Table 4:

TABLE 4

Determination of four distinct hemodynamic patterns and their correlation in patients with diagnosis of cancer and without cancer in the Discovery Group.

| Correlation with diagnosis | Male | | Female | | Total |
|---|---|---|---|---|---|
| | HCC (%) | Healthy control (%) | Breast cancer (%) | Healthy control (%) | |
| Correct correlation | 5 (83.3) | 3 (100.0) | 5 (83.3) | 3 (100.0) | 16 |
| Wrong correlation | 1 (16.7) | 0 | 1 (16.7) | 0 | 2 |
| Total | 6 | 3 | 6 | 3 | 18 |

Discovery of Tumor-Specific Hemodynamic Response Pattern During Exposure Periods:

Each AM RF EMF exposure (HCC-specific, breast cancer-specific, and randomly chosen modulation frequencies) could be tested independently by the computative. A similar hemodynamic response pattern in six (100.0%) of six patients with HCC, which only occurred during exposure to HCC-specific modulation frequencies was observed, seen in Table 5:

TABLE 5

Identification of cancer specific hemodynamic response pattern upon exposure to AM RF EMF modulated at specific and non-specific frequencies in patients with diagnosis of cancer in the Discovery Group.

| Cancer-specific Hemodynamic response pattern | HCC | | | Breast cancer | | |
|---|---|---|---|---|---|---|
| | Cancer-specific frequencies # exposures (%) | Non-cancer specific frequencies # exposures (%) | Total Exposures | Cancer-specific frequencies # exposures (%) | Non-cancer specific frequencies # exposures (%) | Total Exposures |
| Correct correlation | 6 (100.0) | 0 | 6 | 5 (83.3) | 1 (14.3) | 6 |
| Wrong correlation | 0 | 12 (100.0) | 12 | 1 (16.7) | 11 (91.6) | 12 |
| Total | 6 (100.0) | 12 (100.0) | 18 | 6 (100.0) | 12 (100.0) | 18 |

In patients with breast cancer, application of a computative identified a similar hemodynamic response pattern in 5 (83.3%) of six cases, which only occurred during exposure to breast cancer-specific modulation frequencies (Table 2). Hence, in patients with a diagnosis of cancer a tumor-specific hemodynamic response pattern was correctly identified in 11 (91.6%) of 12 exposures to the corresponding tumor-specific modulation frequencies. A tumor-specific hemodynamic response in only one (4%) of 24 exposures to randomly chosen modulation frequencies was observed.

Validation Group and Surgical Group
Validation of Baseline Hemodynamic Pattern Computations:

A correct diagnosis based on baseline hemodynamic pattern was made in 9 (81.8%) of 11 cases of HCC, 12 (85.7%) of 14 cases of breast cancer and 21 (67.7%) out of 31 healthy controls, as seen in Table 6:

TABLE 6

Determination of four distinct hemodynamic patterns and their correlation in patients with diagnosis of cancer and without cancer in the Validation Group.

| Correlation with diagnosis | Male | | Female | | Total |
|---|---|---|---|---|---|
| | HCC (%) | Healthy control (%) | Breast cancer (%) | Healthy control (%) | |
| Correct correlation | 11 (100.0) | 9 (69.2) | 14 (100.0) | 17 (94.4) | 51 |
| Wrong correlation | 0 | 4 (30.8) | 0 | 1 (5.6) | 5 |
| Total | 11 (100.0) | 13 (100.0) | 14 (100.0) | 18 (100.0) | 56 |
| Sensitivity | 100.0% | | 100.0% | | |
| Specificity | | 69.2% | | 94.4% | |

Validation of tumor-specific hemodynamic response pattern during AM RF EMF exposure: The HCC-specific hemodynamic response pattern was identified in 10 (90.0%) of 11 cases of HCC patients (Table 4). The breast cancer-specific hemodynamic response pattern was identified in 12 (85.7%) of 14 female patients with breast cancer, as seen in Table 7:

TABLE 7

Identification of cancer specific hemodynamic response pattern upon exposure to AM RF EMF modulated at specific and non-specific frequencies in patients with diagnosis of cancer in the Validation Group:

| | HCC | | | Breast cancer | | |
|---|---|---|---|---|---|---|
| Cancer-specific Hemodynamic response pattern | Cancer-specific frequencies # exposures (%) | Non-cancer specific frequencies # exposures (%) | Total Exposures | Cancer-specific frequencies # exposures (%) | Non-cancer specific frequencies # exposures (%) | Total Exposures |
| Correct correlation | 6 (100.0) | 0 | 6 | 5 (83.3) | 1 (14.3) | 6 |
| Wrong correlation | 0 | 12 (100.0) | 12 | 1 (16.7) | 11 (91.6) | 12 |
| Total | 6 (100.0) | 12 (100.0) | 18 | 6 (100.0) | 12 (100.0) | 18 |

Female HCC analysis: female patients with HCC were found to have the same hemodynamic pattern and hemodynamic response pattern to AM RF EMF as males with HCC, as seen in Table 8:

TABLE 8

Determination of four distinct hemodynamic patterns and their correlation with diagnosis and determination of cancer specific hemodynamic response pattern upon exposure to AM RF EMF modulated at specific and non-specific frequencies in male and female patients diagnosed with HCC

| Correlation with diagnosis | HCC (%) | Male | Female | Total |
|---|---|---|---|---|
| Correct correlation | 6 (75.0) | 5 | 1 | 6 |
| Wrong correlation | 02 (25.0) | 1 | 1 | 2 |
| Total | 8 (100.0) | 6 | 2 | 8 |

| Cancer-specific Hemodynamic response pattern | Cancer-specific frequencies #exposures (%) | Male Cancer-specific frequencies #exposures | Female Cancer-specific frequencies #exposures | Total #exposures |
|---|---|---|---|---|
| Cancer specific pattern | 8 (100.0) | 6 | 2 | 8 |
| non-cancer pattern | 0 | 0 | 0 | 0 |
| Total exposures | 8 (100.0) | 6 | 2 | 8 |

HCC Specific Hemodynamic Response Pattern Before and after Surgical Resection:

There was no significant change in the hemodynamic patterns during the basal non-exposure period and exposure to randomly chosen and breast cancer-specific modulation frequencies. On the contrary, there was a significant difference between the pre- and the post-resection hemodynamic response pattern during exposure to HCC-specific modulated frequencies in six (100%) of six patients.

Pre-Specified Post-Hoc Analysis:

Combined analysis of all 74 individuals led to the identification of refined hemodynamic pattern criteria. These refined criteria result in better hemodynamic pattern characterization between patients with a diagnosis of cancer and healthy controls. Correlation between hemodynamic pattern and patient diagnosis was achieved in 16 (100.0%) of 16 patient with HCC, 20 (100. 0%) of 20 patients with breast cancer and 32 (86.4%) of 37 healthy controls.

In accordance with the present invention, the identification and characterization of new methods allowing for the diagnosis of hepatocellular carcinoma and breast cancer in a blinded fashion based solely on hemodynamic parameters measured before and during exposure to 27. 12 MHz RF EMF amplitude modulated at tumor-specific frequencies are provided. These findings may have broad clinical implications for the diagnosis of cancer.

While the invention has been described with specific embodiments, other alternatives, modifications, and variations will be apparent to those skilled in the art. Accordingly, it will be intended to include all such alternatives, modifications and variations set forth within the spirit and scope of the appended claims.

What is claimed is:

1. A hemodynamic parameter (Hdp) monitoring system for diagnosing a health condition of a patient, comprising:
    an Hdp monitor that measures and records Hdp values exhibited by the patient during (i) a non-exposure period and (ii) during an exposure period during which the patient is exposed to amplitude-modulated radio-frequency electromagnetic field (EMF) output signals, wherein the Hdp values comprise a pressure component, a flow component and a beat component,
    an electrically-powered generator to generate the amplitude-modulated radio-frequency EMF output signals for exposing or applying to the patient during the exposure period, comprising an amplitude modulation controller for controlling the amplitude of the amplitude-modulated radio-frequency EMF output signals, and
    a storage system comprising predetermined representative Hdp values from one or a plurality of surrogate patients pre-diagnosed with the poor health condition, which storage system is adapted to allow for comparison of the Hdp values of the patient from the (i) basal or non-exposure period and from (ii) during or after the exposure period, with the predetermined representative Hdp values from the one or a plurality of surrogate patients pre-diagnosed with the health condition.

2. The Hdp monitoring system according to claim 1, wherein one or more of the Hdp values are selected from the group comprising:
- systolic blood pressure,
- diastolic blood pressure,
- median blood pressure,
- stroke volume,
- cardiac output,
- total peripheral resistance,
- RR interval,
- heart rate, and
- pulse pressure.

3. The Hdp monitoring system according to claim 1, in which the Hdp monitor is adapted to separately measure and record each of the Hdp values exhibited by the patient during both (i) the non-exposure period and (ii) during the exposure period.

4. The Hdp monitoring system according to claim 1, in which the Hdp monitor is adapted to repeatedly measure and record the Hdp values during a period of time determined by at least ten heart-beat times.

5. The Hdp monitoring system according to claim 1, further comprising a probe connected to the electrically powered generator through which the patient is exposed to the amplitude-modulated radio-frequency EMF output signals during the exposure period.

6. The Hdp monitoring system according to claim 5, in which the probe is an antenna for intrabuccal administration of the amplitude-modulated radio-frequency EMF output signals.

7. The Hdp monitoring system according to claim 1, in which the health condition is a type of cancer.

8. The Hdp monitoring system according to claim 7, in which the type of cancer is hepatocellular carcinoma (HCC) or breast cancer.

9. A method of diagnosing a health condition of a patient, comprising the steps of:
- exposing a patient to amplitude-modulated radio-frequency electromagnetic field (EMF) output signals during an exposure period;
- during the exposure period, measuring and recording, by means of an Hdp monitoring system, Hdp values of a patient;
- during a non-exposure period, measuring and recording, by means of the Hdp monitoring system, the Hdp values of the patient;
- comparing the Hdp values of the patient from the non-exposure period and the exposure period with predetermined representative Hdp values from a non-exposure period and an exposure period from one or a plurality of surrogate patients pre-diagnosed to be healthy and/or from one or a plurality of surrogate patients pre-diagnosed with the health condition; and
- identifying the health condition in the patient;
- wherein the Hdp values comprise a pressure component, a flow component and a beat component.

10. The method of claim 9, wherein one or more of the Hdp values are selected from the group comprising:
- systolic blood pressure,
- diastolic blood pressure,
- median blood pressure,
- stroke volume,
- cardiac output,
- total peripheral resistance,
- RR interval,
- heart rate, and
- pulse pressure.

11. The method of claim 9, in which the health condition is a type of cancer.

12. The method of claim 11, in which the type of cancer is hepatocellular carcinoma (HCC) or breast cancer.

* * * * *